United States Patent [19]
Marlow et al.

[11] Patent Number: 5,368,606
[45] Date of Patent: Nov. 29, 1994

[54] ENDOSCOPIC INSTRUMENT SYSTEM

[75] Inventors: Scott C. Marlow, Chesterland; Haans K. Petruschke, Kirtland; Donald B. Coon, Chesterland; John T. Nelson, Kirtland, all of Ohio

[73] Assignee: Marlow Surgical Technologies, Inc., Willoughby, Ohio

[21] Appl. No.: 907,853

[22] Filed: Jul. 2, 1992

[51] Int. Cl.⁵ .............................................. A61B 17/32
[52] U.S. Cl. .................................. 606/170; 606/174; 606/207
[58] Field of Search ............... 128/751, 752, 753, 754, 128/755; 604/22; 606/37, 39, 45, 46, 51, 52, 99, 151, 167, 170, 171, 174, 205, 175, 207

[56] References Cited

U.S. PATENT DOCUMENTS

| | | | |
|---|---|---|---|
| 1,127,948 | 2/1915 | Wappler | 606/170 |
| 1,274,669 | 8/1918 | Bohn . | |
| 2,113,246 | 4/1938 | Wappler . | |
| 2,114,695 | 4/1938 | Anderson . | |
| 2,790,437 | 4/1957 | Moore | 606/170 |
| 3,837,345 | 9/1974 | Matar . | |
| 4,084,594 | 4/1978 | Mosior . | |
| 4,122,856 | 10/1978 | Mosior et al. . | |
| 4,258,716 | 3/1981 | Sutherland . | |
| 4,569,131 | 2/1986 | Falk et al. . | |
| 4,646,751 | 3/1987 | Maslanka | 128/751 |
| 4,721,116 | 1/1988 | Schintgen et al. | 128/751 |
| 4,971,067 | 11/1990 | Boldue et al. . | |
| 5,053,043 | 10/1991 | Gottesman . | |
| 5,133,735 | 7/1992 | Slater et al. | 128/751 |
| 5,147,357 | 9/1992 | Rose et al. | 606/52 |
| 5,147,373 | 9/1992 | Ferzli . | |
| 5,172,700 | 12/1992 | Bencini et al. | 606/207 |
| 5,282,806 | 2/1994 | Haber et al. | 606/207 |
| 5,304,203 | 4/1994 | El-Mallawany et al. | 128/751 |
| 5,308,358 | 5/1994 | Bond et al. | 606/207 |

FOREIGN PATENT DOCUMENTS

| | | |
|---|---|---|
| 1089924 | 9/1960 | Germany . |
| 9007356 | 5/1991 | Germany . |
| 2140735 | 12/1984 | United Kingdom . |
| 9102493 | 3/1991 | WIPO . |
| 9217116 | 10/1992 | WIPO . |

*Primary Examiner*—C. Fred Rosenbaum
*Assistant Examiner*—N. Kent Gring
*Attorney, Agent, or Firm*—Thompson, Hine & Flory

[57] ABSTRACT

An endoscopic instrument system which includes a handle portion with a scissors grip, a shaft extending from the scissors grip and shaped to extend through a cannula, and a plurality of disposable end tools, each mountable on the end of the shaft and actuatable by the scissors handle. In a preferred embodiment, the scissors handle actuates a rod extending through the shaft which is connected to the end tool. The end tool includes a pair of jaws pivotally mounted on the support and connected to a reciprocating stub shaft by links. The stub shaft is connected to the actuating rod of the handle portion so that movement of the scissors handle causes the jaws to pivot relative to each other. The end tool may take the form of a scissor, grasper, biopsy or dissector, depending upon the specific shape of the jaws. An advantage of the invention is that the support of the end tools is made of a relatively inexpensive plastic material such that the end tools may be discarded when the jaws become dull, thus obviating the need for repeated cleaning and sharpening and eliminating the most difficult portion to clean.

32 Claims, 2 Drawing Sheets

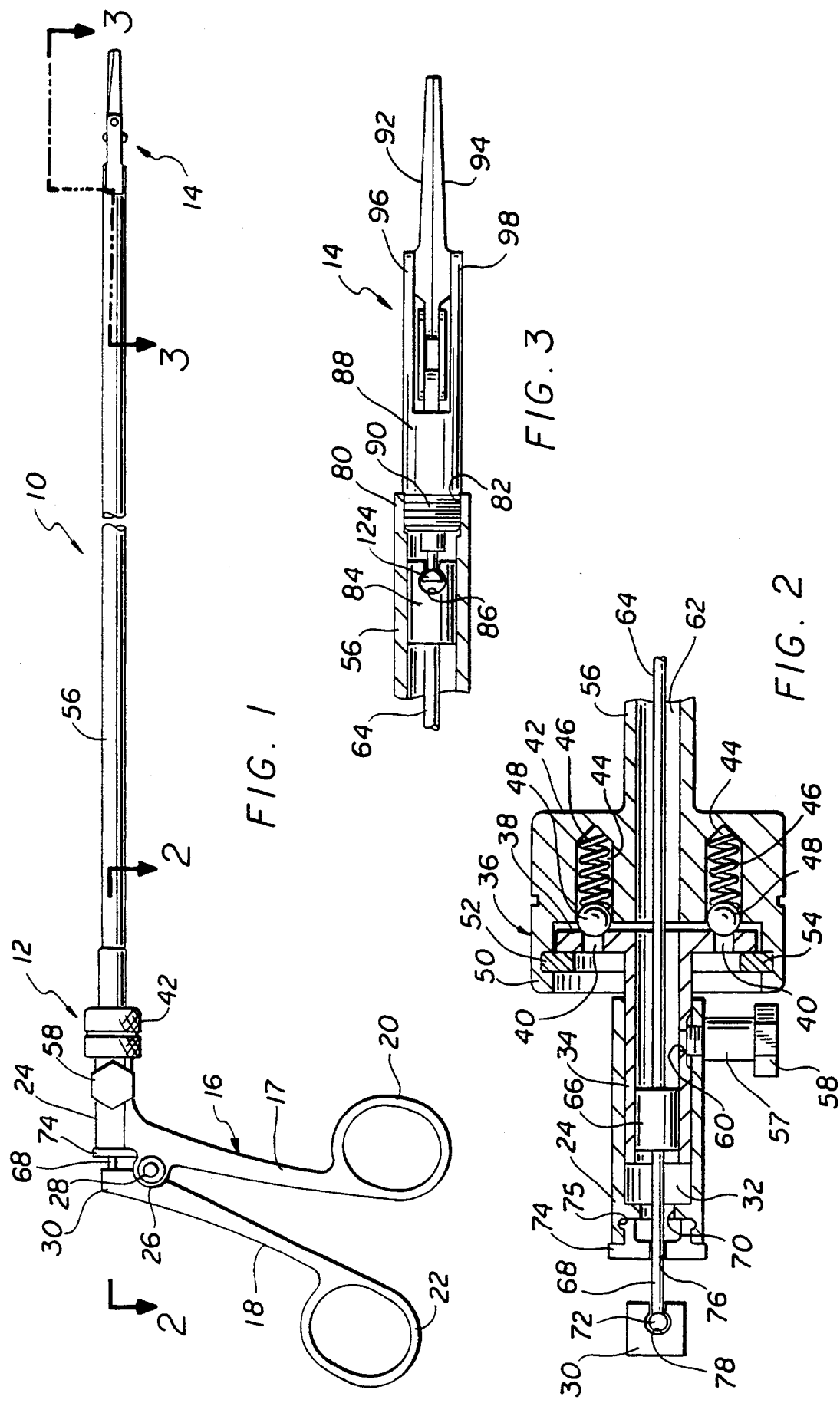

ENDOSCOPIC INSTRUMENT SYSTEM

BACKGROUND OF THE INVENTION

The present invention relates to surgical instruments and, more particularly, to endoscopic instruments suitable for use with a trocar or cannula.

A branch a endoscopic surgery is laparoscopic surgery which involves the use of a cannula that is inserted through an incision in the skin of the subject to provide access to an internal cavity, such as the thoracic cavity. An example of such a cannula is disclosed in Hasson U.S. Pat. No. 5,002,557, the disclosure of which is incorporated herein by reference. Surgery is performed with a laparoscopic instrument, which typically includes a scissors handle and an elongate shaft terminating in a pair of pivoting jaws. The handle includes a scissors or pliers grip which, when squeezed and released, reciprocates a rod extending through the shaft to pivot the jaws. The jaws and shaft are sized to be inserted through the cannula into the body cavity where the surgery is to be performed. Similar devices are employed in thoroscopic and arthroscopic surgery.

As with any surgical instrument, should the tool include sharpened jaws for cutting, it is desirable to maintain the sharpened edges as sharp as possible for each operation. Further, it is also desirable to design the instrument so that it can be easily and thoroughly cleaned after each operation. However, a disadvantage with unitary instruments; that is, instruments in which the handle, shaft and cutting tool are permanently attached to each other, is that cleaning of the instrument and sharpening of the tool after each operation becomes time-consuming and costly.

Accordingly, attempts have been made to provide laparoscopy instruments which minimize the time and expense of cleaning and sharpening. For example, some laparoscopy instruments are made in which substantially the entire instrument is constructed of plastic, except for the shaft rod and jaws, so that the entire instrument is disposable after each operation. Alternately, instruments such as those disclosed in Falk et al. U.S. Pat. No. 4,569,131 are designed in which the handle is separable from the shaft and jaws, so that the unitary shaft, jaws and rod may be disposed after each use, or cleaned and sharpened separately from the handle. A disadvantage with these types of designs is that the disposable component—whether it be the entire instrument or only the shaft and cutting tool—provides an undesirably high volume of medical waste which requires special disposal procedures. Further, disposable instruments made largely of plastic are somewhat flimsy and difficult to maneuver.

Accordingly, there is a need for a laparoscopy instrument which eliminates the need for repeated sharpening of the cutting surfaces of the instrument and which facilitates cleaning and reduces cross contamination potential.

SUMMARY OF THE INVENTION

The present invention is an endoscopic instrument system which includes a handle portion having a elongate shaft for insertion through a cannula and a plurality of end tools, each attachable to the end of the shaft. In the preferred embodiment, each of the end tools includes pivoting jaws which actually contact the tissue of the subject during the operation. The end tools preferably include plastic components which lower their cost, and are disposable. One advantage of the present invention is that the disposable component of the entire instrument is relatively small, thereby minimizing the cost of using the instrument over several operations and minimizing the volume of medical waste comprised by the disposable components of the instrument.

In a preferred embodiment, the handle portion includes pivoting scissor handles and an actuating rod which extends through the shaft. The rod terminates in a clevis which receives the hemispherical tip of a stub shaft that is reciprocatably mounted within the end tool. The stub shaft is connected to a pair of pivoting jaws by links so that reciprocal movement of the stub shaft causes the jaws to pivot relative to the end tool in a scissors fashion.

The end tool includes a support which is made of a glass fiber reinforced plastic and threads onto the open end of the handle shaft. The pivoting jaws of the end tools may be formed to perform a variety of tasks; for example, the jaws can be in the form of scissors, graspers, biopsy, or dissectors.

Another advantage of the present invention is that only the portions of the instrument which become most contaminated during an operation and are most difficult to clean; namely, the jaws and linkage operating the jaws, are disposed of with the end tool. In the preferred embodiment, a cleaning port extends through the handle portion and facilitates the flushing of the shaft with an appropriate liquid cleaning agent after each operation. A direct result of incorporating the laparoscopy instrument of the present invention in a hospital operating room procedure is that a relatively few handle portions need be present while having a relatively large number of end tools, in contrast to prior procedures in which an extensive array of unitary instruments must be present. Further, each surgeon may be provided with a set of end tools, each performing a different function, and each selected from an array of end tools to suit the particular surgeon's needs and preferences.

Accordingly, it is an object of the present invention to provide an endoscopic instrument system which eliminates the need for repeatedly sharpening the cutting jaws of the instrument; an instrument system in which the linkage components which are the most difficult to clean are disposable, thereby obviating the necessity for repeated cleaning; an instrument system in which the shaft portion is easily cleaned after each operation; an instrument system in which the cutting surfaces and linkages are disposable such that the volume of disposed equipment is minimized; an instrument system having a disposable cutting element in which the support component is made of a relatively inexpensive plastic material; an instrument system having a plurality of attachable end tools which can be customized for a particular practitioner or application; and an instrument system which is relatively easy to manufacture and utilize.

Other objects and advantages of the present invention will be apparent from the following description, the accompanying drawing and the appended claims.

BRIEF DESCRIPTION OF THE DRAWING

FIG. 1 is a side elevation of the handle portion and one end tool of a preferred embodiment of the endoscopic instrument system of the present invention;

FIG. 2 is a section taken at line 2—2 of FIG. 1;

FIG. 3 is a section taken at line 3—3 of FIG. 1;

DETAILED DESCRIPTION

Figure 4:
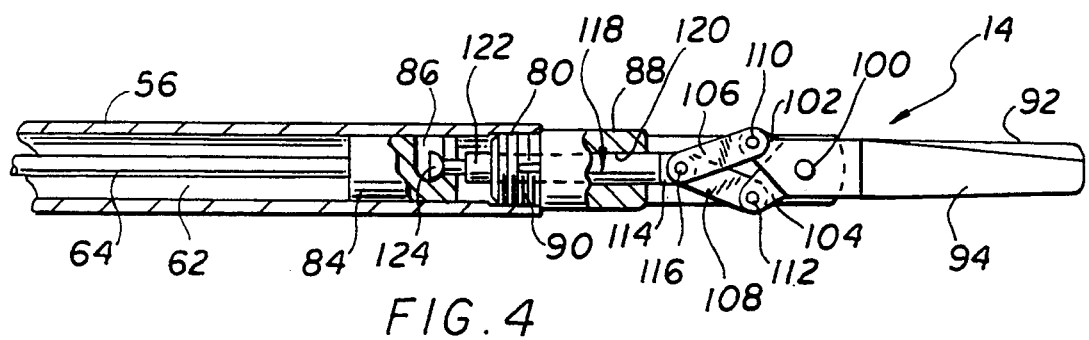
FIG. 4 is a detail of the instrument of FIG. 1 showing the shaft end in section and a portion of the end tool broken away.

As shown in FIG. 1, the endoscopic instrument system of the present invention, generally designated 10, includes a handle portion, generally designated 12, and an end tool, generally designated 14. The handle portion 12 includes a scissors component 16 which is gripped by the user and has front and rear scissors handles 17, 18, respectively. Scissors handles 17 and 18 include finger loops 20, 22.

Scissors handle 17 is attached to a cylindrical housing 24 and includes a clevis 26 which is engaged by scissors handle 18 and secured by a screw 28. When scissor handle 18 is pivoted relative to handle 16 about screw 28, the upper end 30 of handle 18 reciprocates relative to the housing 24.

As shown in FIG. 2, the housing 24 includes a hollow interior 32 which receives an inner sleeve 34 of a rotatable coupling 36. The inner sleeve 34 includes a flange 38 having a plurality of orifices 40 spaced about its periphery. The coupling 36 includes a coupling body 42 having a plurality of cylindrical cavities 44, each receiving an extension spring 46 which urges a ball 48 against an adjacent one of the orifices 40. The balls 48 are larger in diameter than the orifices so that the orifices merely provide seats for the balls 48. The inner end 50 of the coupling body 36 includes an annular groove 52 which receives a split ring 54. The split ring 54 retains the coupling body 42 on the flange 38. The body 42 is unitary with a hollow, elongate shaft 56 (see also FIG. 1). While the shaft 56 of the preferred embodiment is made of surgical stainless steel, it is within the scope of the invention to provide a flexible shaft.

The external surface of the body 42 is knurled to facilitate grasping by a user. The coupling 36 enables the shaft 56 to be rotated relative to the housing 24 of the handle portion 12, and the engagement of ball 48 and orifices 40 provide detent stops.

The housing portion 24 includes a lateral tube 57 which is capped by a removable nut 58 and communicates with the interior 32 of the housing. The tube 57 extends through an opening 60 in the sleeve 34 to communicate with the interior 62 of the coupling 36 and shaft 56.

The handle portion 12 includes a rod 64 which extends through the interiors 62, 32 of the shaft 56 and housing 24, respectively. The rod includes an enlarged, cylindrical segment 66 which engages the interior or internal wall of the sleeve 34 for location purposes and a rear segment 68 which protrudes through an end opening 70 in the housing 24 to terminate in a spherical end 72. The housing 24 includes a plastic end cap 74 mounted in a dovetail slot 75 which provides a seal about the extension 68. The extension 68 passes through an orifice 76 in the cap and the end 72 of the extension is received within a clevis 78 formed in the upper end 30 of the handle 18. Consequently, pivoting movement of the handle 18 relative to handle 17 causes the upper end 30 to reciprocate relative to the housing 24, causing the rod 64 to reciprocate relative to the handle portion 12.

As shown in FIG. 3, the outer end 80 of the shaft 56 includes a threaded interior surface 82. The end 84 of the rod 64 includes a clevis 86. The end tool 14 includes a support 88, preferably made of a glass filled plastic, such as 40% glass filled polyetherimide. Other plastics include polyethersulfone and polyetheretherketone. Support 88 has a threaded inner end 90 which is shaped to thread into the threaded interior 82 of the end 80 of shaft 56. The support 88 mounts a pair of jaws 92, 94, which are best shown in FIG. 4.

The support 88 includes a pair of arms 96, 98 (see FIG. 3) which receive a rivet 100 that mounts the jaws 92, 94 for pivotal movement relative to the support and to each other. The jaws 92, 94 each include ears 102, 104 which are pivotally attached to links 106, 108 by rivets 110, 112. The links 106, 108 are, in turn, pivotally attached to a knuckle 114 by a rivet 116. The knuckle 114 forms a portion of a stub shaft 118 which is slidably mounted within a passage 120 formed in the support 88. The stub shaft is sized such that an inner end 122 protrudes rearwardly from the threaded end 90 and terminates in a hemispherical tip 124 which is shaped to be seated within the clevis 86.

Figure 5:
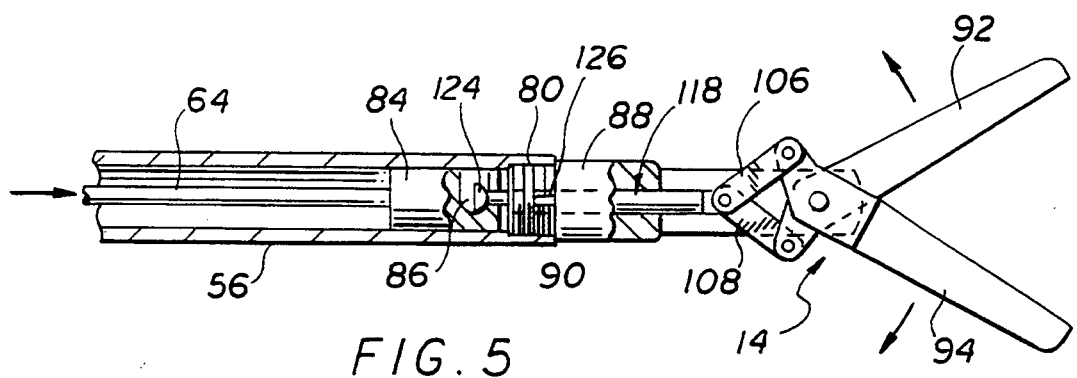
FIG. 5 is the detail of FIG. 4 in which the tool jaws have been pivoted to an open position.

As shown in FIG. 5, displacement of the rod 64 relative to the shaft 56 by pivoting the handles 17, 18 in the manner previously described causes the end 84 of the rod to displace the stub shaft 118 outwardly relative to the support 88. This outward displacement causes the links 106, 108 to pivot the jaws 92, 94 outwardly away from each other. Conversely, displacement of the rod 64 inwardly, caused by squeezing the handles 17, 18 together (see FIG. 1), causes the stub shaft 118 to be displaced inwardly relative to the support 88, so that the links 106, 108 draw the jaws 92, 94 together. Consequently, pivotal movement of handle 18 relative to handle 17 causes the jaws 92, 94 to pivot relative to each other.

To remove the end tool 14 from the shaft 56, the support 88 is first threaded out of the threaded end 80 of the shaft 56. The loops 20, 22 of the handles 17, 18 are drawn together, which displaces the rod end 84 outwardly from the shaft end 80, exposing the clevis 86. Once the rod end 84 clears the shaft end 80, the tip 124 of the stub shaft 118 can be removed from the clevis 86 and the entire end tool 14 discarded. It is not necessary to remove the rod 64 from the handle portion 12 or disconnect the extension 68 from the handle upper end 30.

Reattachment of a fresh end tool 14 is accomplished by reversing the aforementioned sequence of steps. Specifically, a fresh tool 14 is placed adjacent to the shaft end 80 and the tip 124 placed into the clevis 86. The handles 17, 18 are spread slightly and the support 88 is threaded into the shaft end 80. In the preferred embodiment, the threaded end 90 of the support 88 includes bosses 126 which are deformed by the threads of the threaded end 80 to prevent the inadvertent unthreading of the end tool 14.

To clean the handle portion 12 of the instrument system 10, the tip 14 is first removed as previously described. Then, the nut 58 is removed from the tube 57 and a cleaning solvent is flushed through the interiors 32, 62 of the housing 24 and shaft 56 so that the solvent exists the end 80 of the shaft, thereby flushing any debris from the shaft. However, it should be noted that the connection of the tip 14 with the shaft end 80 minimizes the entry of contaminants within the interior 62, since the only openings are the seam between the shaft end and support 88 and the passage 120 and stub shaft 118.

Figure 6:
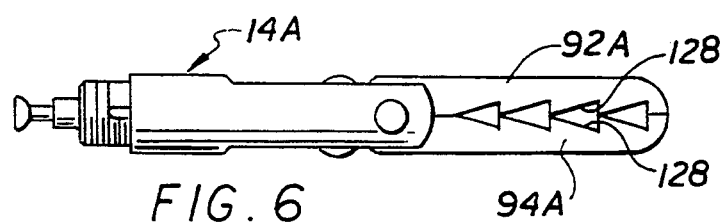
FIG. 6 is a side elevation of a gripper end tool of the present invention.
Figure 7:
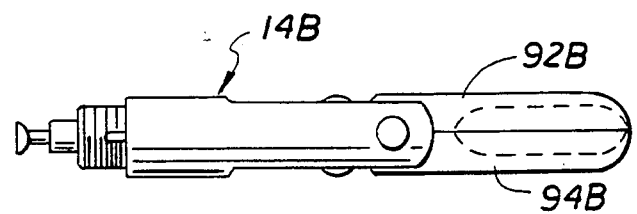
FIG. 7 is a side elevation of a biopsy end tool of the present invention.
Figure 8:
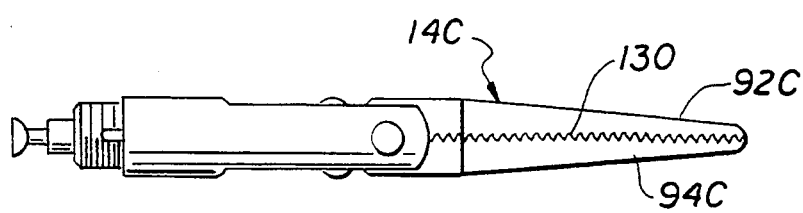
FIG. 8 is a side elevation of a dissector end tool of the present invention.

FIGS. 6, 7 and 8 show alternate embodiments of the end tool 14A, 14B, 14C, each designed to perform a specialized function and forming a component of the system 10. In 14A, the jaws 92A, 94A include rear-facing sawtooth edges 128 such that the tip 14A forms an alligator grasper. In FIG. 7, the end tool 14B includes jaws 92B, 94B which are shaped to form a biopsy. In FIG. 8, the end tool 14C includes jaws 92C, 94C having sawtooth edges 130 to form a dissector.

While the form of apparatus herein described constitute a preferred embodiment of the invention, it is to be understood that the invention is not limited to this precise form of apparatus, and that changes may be made therein without departing from the scope of the invention.

What is claimed is:

1. An endoscopic instrument system comprising:
   an instrument including a handle portion having means for gripping said instrument, means forming a shaft extending from said gripping means and means for actuating said instrument, said actuating means including a rod extending from said gripping means, and said gripping means being connected to actuate said rod of said actuating means;
   an instrument end tool, said end tool being connectable to said shaft end by a threaded engagement and including means for engaging said actuating means, said actuating means extending through said shaft from said gripping means to said end tool such that said end tool engages said rod, whereby said end tool is operable by said actuating means; and
   said instrument end tool including link means terminating in an enlarged end, said actuating means including means for releasably engaging said enlarged end.

2. The system of claim 1 wherein each of said end tools includes a support attachable to said shaft end and receiving said link means, a first element pivotally attached to said support and to said link means and a second element attached to said support, whereby movement of said link means in response to movement of said actuating means causes said first element to pivot relative to said support and to said second element.

3. The system of claim 2 wherein said link means includes a stub rod having said enlarged end and being slidably received in said support, and a first link element interconnecting said stub rod and said first element, whereby sliding movement of said stub rod is transmitted through said link element to pivot said first element.

4. The system of claim 3 wherein said second element is pivotally attached to said support, and said link means includes a second link element interconnecting said stub rod and said second element, whereby said sliding movement of said stub rod causes said first and second elements to pivot relative to each other in a scissors movement.

5. The system of claim 4 wherein said first and second elements comprise first and second jaws, respectively, of a scissors.

6. The system of claim 4 wherein said first and second elements comprise first and second jaws, respectively, of a dissector.

7. The system of claim 4 wherein said first and second elements comprise first and second jaws, respectively, of a grasper.

8. The system of claim 4 wherein said first and second end elements comprise first and second jaws, respectively, of a biopsy.

9. The system of claim 1 wherein said engaging means includes clevis means for receiving said enlarged end of an attached one of said end tools.

10. The system of claim 9 wherein said shaft is rotatably mounted on said gripping means.

11. The system of claim 9 wherein said shaft is removable from said gripping means.

12. The system of claim 1 wherein said gripping means includes port means for flushing said shaft.

13. The system of claim 12 wherein said port means includes a stub tube threaded into said gripping means communicating with said shaft.

14. The system of claim 1 further comprising a plurality of said end tools, each being attachable to and detachable from a distal end of said shaft.

15. The system of claim 14 wherein each of said end tools is shaped to perform a function different from others of said end tools.

16. The system of claim 1 wherein said end tools include scissors.

17. For use with an endoscopic instrument of a type having a handle portion including means for gripping said instrument, means forming an elongate shaft extending from said gripping means and having an open end opposite said griping means and means for actuating said instrument, a disposable end tool comprising:
   means forming a pair of jaws; and
   means for supporting said jaw means such that said jaw means move relative to each other, said support means being shaped for removable attachment to an associated shaft end such that said actuating means moves said jaw means and said end tool is replaceably removable from said shaft end without damage to said shaft end, said support means including an inner end adapted to mount on said shaft end;
   said jaw means including a stub shaft slidably mounted on said support means and adapted to engage said actuating means.

18. The end tool of claim 17 wherein said stub shaft includes an end protruding from said inner end and shaped to engage said actuating means.

19. The end tool of claim 18 wherein said jaw means includes first and second jaws, said jaws being pivotally attached to said support means.

20. The end tool of claim 19 wherein said jaw means includes first and second links interconnecting said first and second jaws, respectively, with said stub shaft, whereby reciprocating movement of said stub shaft relative to said support means in response to said actuating means causes said jaws to pivot relative to each other.

21. The end tool of claim 19 wherein said jaws form a scissors.

22. The end tool of claim 19 wherein said jaws form a grasper.

23. The end tool of claim 19 wherein said jaws form a biopsy.

24. The end tool of claim 19 wherein said jaws form a dissector.

25. The end tool of claim 17 wherein said support means is made of a plastic material.

26. The end tool of claim 25 wherein said plastic material is selected from the group consisting of: a glass filled polyetherimide, a glass filled polyetheretherketone and a glass filled polyethersulfone.

27. The end tool of claim 17 wherein said support means includes an inner end adapted to mount on said shaft end.

28. For use with an endoscopic instrument of a type having a handle portion including means for gripping said instrument, an elongate shaft extending from said gripping means and having an open distal end opposite said gripping means and rod means for actuating said instrument, a disposable end tool comprising:
- means forming an end implement;
- means for supporting said end implement such that said end implement moves relative to said supporting means, said supporting means being attachable to a shaft end such that an associated rod means moves said end implement;
- said support means including an inner end adapted to mount on an associated shaft end; and
- said end implement including a stub shaft slidably mounted in said support means and adopted to engage said rod means, said stub shaft including an end protruding from said inner end and shaped to engage said rod means, whereby attachment and detachment of said stub shaft to rod means at a distal end of an associated shaft is facilitated.

29. The end tool of claim 28 wherein said stub shaft is shaped to engage an associated rod means such that axial but not rotational movement is transmitted from associated rod means to said stub shaft.

30. For use with an endoscopic instrument of a type having a handle portion including means for gripping said instrument, means forming an elongate shaft extending from said gripping means and having a threaded open end opposite said gripping means, rod means for actuating said instrument, said rod means being mounted within said shaft for slidable movement by said gripping means and having a clevis end adjacent said shaft end, a disposable end tool comprising:
- a support having a threaded inner end shaped to be threaded into said shaft end;
- a stub shaft mounted within said support for reciprocal movement and having an enlarged end protruding from said inner end shaped to releasably engage an associated clevis end;
- first and second links pivotally attached to said stub shaft within said support;
- first and second jaws pivotally mounted on said support to effect a scissors movement, said first and second jaws being pivotally connected to said first and second links, respectively, whereby reciprocating movement of associated rod means reciprocates said stub shaft and effects said scissors movement of said jaws.

31. For use with an endoscopic instrument of a type having a handle portion including means for gripping said instrument, an elongate shaft extending from said gripping means and having an open distal end opposite said gripping means and rod means for actuating said instrument, a disposable end tool comprising:
- means forming an end implement;
- means for supporting said end implement such that said end implement moves relative to said supporting means, said supporting means being attachable to a shaft end such that an associated rod means moves said end implement relative to said supporting means;
- said supporting means including an inner end adapted to mount on an associated shaft end; and
- said end implement including a stub shaft, said stub shaft being shaped to attach to an associated rod means by a substantially radially inward motion of said stub shaft relative to said rod means.

32. For use with an endoscopic instrument of a type having a handle portion including means for gripping said instrument, an elongate shaft extending from said gripping means and having an open distal end opposite said gripping means and rod means for actuating said instrument, a disposable end tool comprising:
- means forming an end implement;
- means for supporting said end implement such that said end implement moves relative to said supporting means, said supporting means being attachable to a shaft end such that an associated rod means moves said end implement relative to said supporting means;
- said supporting means including an inner end adapted to mount on an associated shaft end; and
- said end implement including a stub shaft, said stub shaft being shaped to be axially but not rotationally coupled to an associated rod means at a distal end of an associated shaft.

* * * * *